United States Patent [19]

Castel et al.

[11] Patent Number: 5,086,788

[45] Date of Patent: Feb. 11, 1992

[54] HAND-HELD PHYSIOLOGICAL STIMULATION APPLICATOR

[76] Inventors: John C. Castel; Alexander Bally, both of c/o Physio Technology, Inc., 1925 W. 6th St., Topeka, Kans. 66606

[21] Appl. No.: 206,440

[22] Filed: Jun. 13, 1988

[51] Int. Cl.⁵ .............................................. A61N 1/00
[52] U.S. Cl. .................................... 128/800; 128/783; 128/24.5
[58] Field of Search ............... 128/783, 800, 802, 790, 128/24.1, 24 A, 24.2, 24.3, 24.4, 24.5, 804, 303.14, 303.17, 303.13, 303.18, 801, 421, 56, 60, 44, 45, 46; 604/22, 20; 606/41, 42

[56] References Cited

U.S. PATENT DOCUMENTS

| | | | |
|---|---|---|---|
| 2,838,672 | 6/1958 | Paust | 250/36 |
| 3,219,029 | 11/1965 | Richards et al. | 128/420 R |
| 3,374,784 | 3/1968 | Brent et al. | 128/46 |
| 3,841,306 | 10/1974 | Hallgren | 128/1.5 |
| 4,112,923 | 9/1978 | Tomecek | 128/1.3 |
| 4,197,851 | 4/1980 | Fellus | 128/422 |
| 4,232,678 | 11/1980 | Skovajsa | 128/395 |
| 4,315,503 | 2/1982 | Ryaby et al. | 128/1.5 |
| 4,431,000 | 2/1984 | Butler et al. | 128/421 |
| 4,453,547 | 6/1984 | Castel et al. | 128/421 |
| 4,532,938 | 8/1985 | Carlisle | 128/801 |
| 4,535,777 | 8/1985 | Castel | 128/421 |
| 4,587,957 | 5/1986 | Castel | 128/1.3 |
| 4,690,141 | 9/1987 | Castel et al. | 128/396 |
| 4,722,326 | 2/1988 | Ruderian | 128/24.1 |

FOREIGN PATENT DOCUMENTS 881837 11/1961 United Kingdom ............. 128/24 A

*Primary Examiner*—Lee S. Cohen
*Assistant Examiner*—S. Getzow
*Attorney, Agent, or Firm*—Wood, Phillips, Mason, Recktenwald & VanSanten

[57] ABSTRACT

A hand-held physiological stimulation and treatment signal applicator. The applicator includes a housing having a portion in which electrical controls are mounted for facilitated manipulation thereof by the user's hand embracing the housing portion in the use of the apparatus. Different types of physiological treatment signals may be provided separately or in combination from the associated power sources and controlled by the housing mounted controls. The applicator head provided for facial engagement with the patient's tissue is swivelly mounted to the end of the applicator housing for facilitated adjustment of the head to insure desired facial engagement between the head and patient's tissue. Structure is provided for providing positive grasping of the applicator housing adjacent the applicator head while preventing interference between the user's fingers and the patient's tissue adjacent the head.

29 Claims, 2 Drawing Sheets

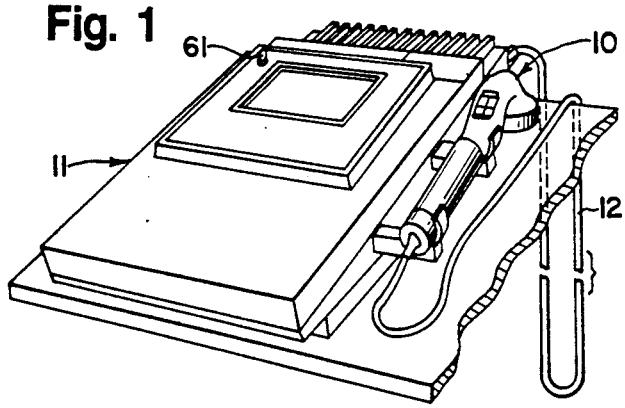
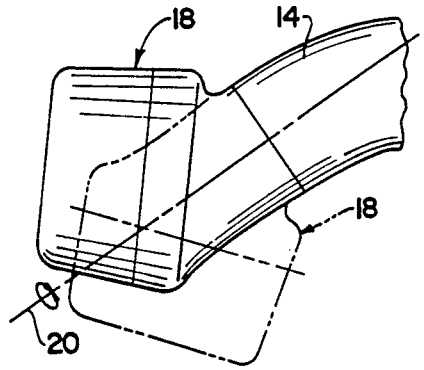
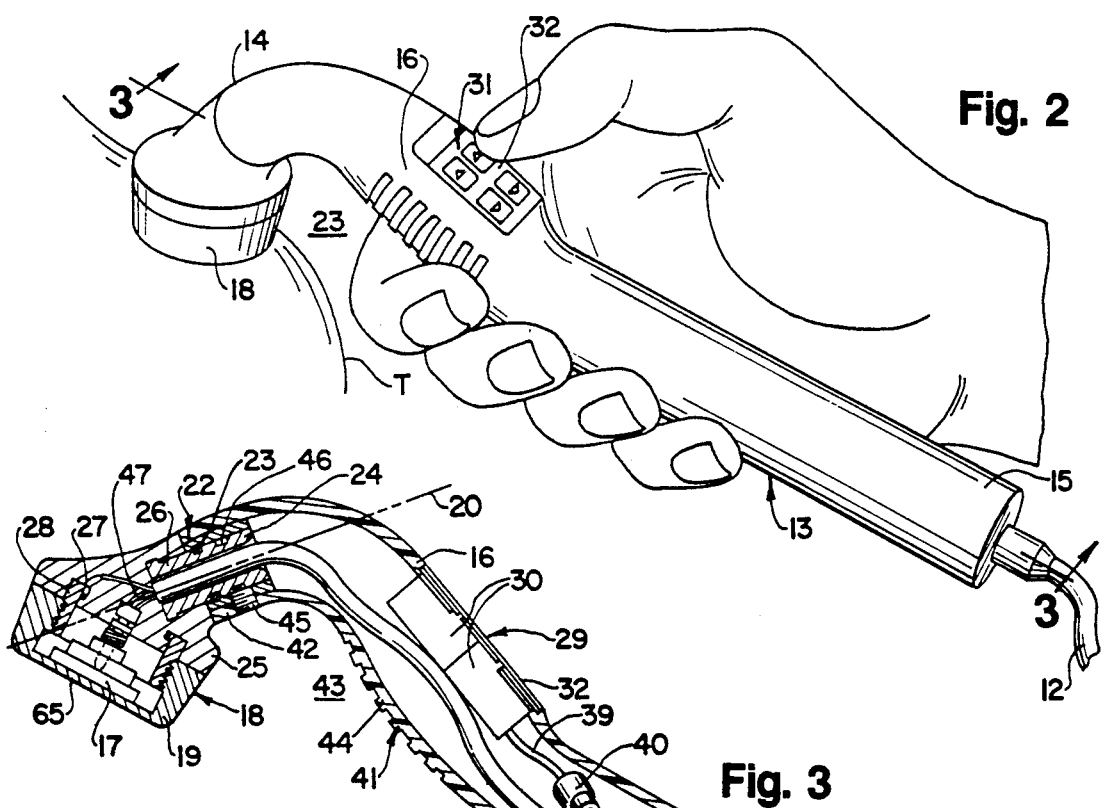
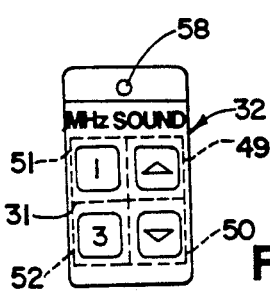
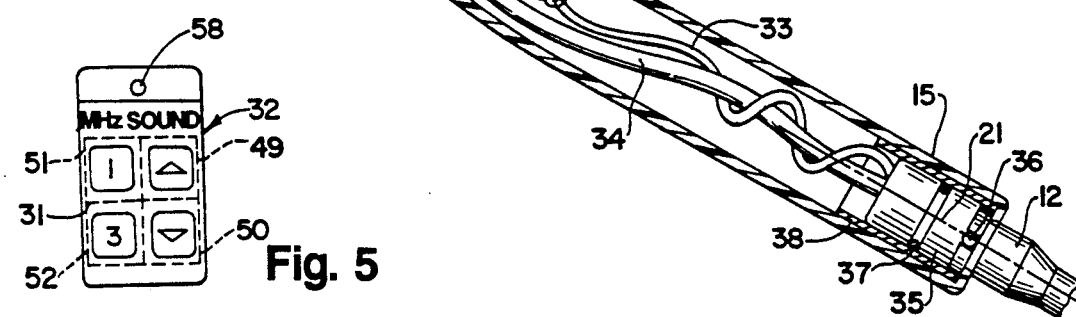

HAND-HELD PHYSIOLOGICAL STIMULATION APPLICATOR

TECHNICAL FIELD

This invention relates to physiological stimuli applicators and in particular to hand-held physiological stimulation applicators.

BACKGROUND ART

In one form of conventional physiological stimulation applicator, a power source adapted to provide high frequency sound vibrations is provided with a transducer adapted to be electrically operated for producing mechanical vibrations at high frequency suitable to provide physiological stimulation and/or treatment of a patient's tissue.

It is further known to provide such an apparatus wherein electrical stimulation of the patient's tissue is effected by means of the transducer.

It is conventional in such known apparatuses to provide the power oscillator and amplifier, as well as controls for controlling the power and frequency of the applied signals, in a base unit. A hand-held signal applicator is connected to the base unit by suitable electrical conductors and includes, at an end portion thereof, the transducer adapted to be urged against the patient's tissue for delivering the stimulation and/or treatment oscillation to the tissue.

Suitable controls are provided on the base unit for selecting different power levels and frequencies, as desired.

DISCLOSURE OF INVENTION

The present invention comprehends an improved applicator for providing such high frequency oscillations either in the form of mechanical vibrations or electrical stimulation signals to the patient's tissue.

The invention comprehends the provision of a manually operable apparatus for controlled physiological stimulation which includes an elongated housing having a first end defining an axis, an opposite second end, and a grasping portion intermediate the ends, an electrically operable transducer, mounting means for mounting the transducer to the first housing end, and means for energizing the transducer including a power source spaced from the housing, manually operable controls at the housing grasping portion, and electrical conductors for interconnecting the power source, controls, and transducer to permit concurrent controlled energization and physical positioning of the transducer by a user's hand embracing the housing grasping portion.

Further, the invention comprehends the provision of such an applicator which includes an elongated housing having a first end defining an axis, an opposite second end, and a grasping portion intermediate the ends, an electrically operable transducer, mounting means for mounting the transducer to the first housing end comprising means for directing the transducer at an angle to the axis selectively at any one of a plurality of portions circumferentially about the axis, and means for energizing the transducer including a power source, manually operable controls, and electrical conductors for interconnecting the power source, controls, and transducer to permit physical positioning of the transducer by a user's hand embracing the housing grasping portion with the transducer positioned at a preselected angle to the axis.

In the illustrated embodiment, the applicator includes both mounting means for mounting the transducer to the first housing end comprising means for directing the transducer at an angle to the axis selectively at any one of a plurality of positions circumferentially about the axis, and means for energizing the transducer including a power source spaced from the housing manually operable controls at the housing grasping portion, and electrical conductors for interconnecting the power source, controls, and transducer to permit concurrent controlled energization and physical positioning of the transducer by a user's hand embracing the housing grasping portion.

The controls may comprise means for controlling the power and/or the frequency of the electrical oscillations delivered from the power source.

The controls may be arranged to provide discrete power or frequency outputs from the power source, as desired.

In the illustrated embodiment, the transducer defines a planar tissue-engaging surface extending at an angle of substantially 45° to the longitudinal axis of the first end of the housing.

In the illustrated embodiment, the grasping portion defines an axis extending substantially perpendicular to the housing first end axis.

In the illustrated embodiment, the grasping portion includes means defining an irregular grasping surface for improved slip-free grasping of the grasping portion of the housing.

In the illustrated embodiment, the housing grasping portion defines a C-shaped portion providing a fingertip receiving space adjacent the housing first end for facilitated application of the tissue stimulation vibrations or oscillations.

The hand-held physiological stimulation applicator of the present invention is extremely simple and economical of construction, while yet providing for improved facilitated provision of physiological vibrations and/or electrical signals to the patient's tissue under improved control thereof by the user.

BRIEF DESCRIPTION OF THE DRAWING

Other features and advantages of the invention will be apparent from the following description taken in connection with the accompanying drawing wherein FIG. 1 is a perspective view of a physiological stimulation apparatus embodying the invention;

FIG. 2 is a perspective view of the hand-held applicator thereof;

FIG. 3 is a longitudinal section of the applicator;

FIG. 4 is a side elevation illustrating the repositioning of the applicator head about the longitudinal axis of the first end of the applicator housing;

FIG. 5 is a plan view of the control buttons on the grasping portion of the housing;

BEST MODE FOR CARRYING OUT THE INVENTION

Figure 6:
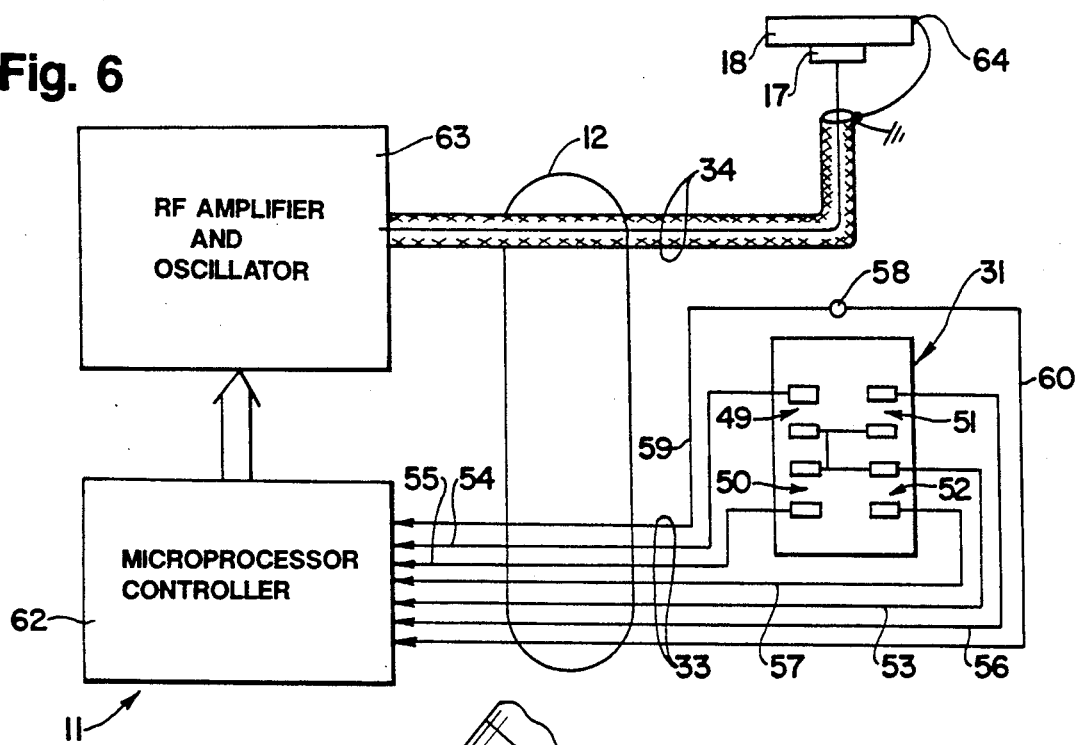
FIG. 6 is a schematic electrical diagram illustrating the electrical connections of the apparatus.

In the illustrative embodiment of the invention as disclosed in the drawing, a physiological stimulation applicator, generally designated 10, is connected to a power source 11 by a flexible electrical conductor cable 12. The applicator is adapted to be hand-held for application of physiological stimulation signals, such as ultrasound or electrical stimulation signals to the tissue of a patient.

Applicator 10 includes a watertight outer housing 13 defining a first end 14, an opposite, second end 15, and a grasping portion 16 intermediate ends 14 and 15.

A transducer 17 (see FIG. 3) is mounted within a swivel head 18 on end 14 of the housing.

In the illustrated embodiment, the transducer comprises a conventional crystal adapted to provide ultrasonic vibrations as a result of the application of ultrasonic high frequency electrical current thereto. As further shown in FIG. 3, head 18 includes a distal cap 19 through which the mechanical vibrations are provided from the crystal to a patient's tissue T. In the illustrated embodiment, the cap 19 is formed of a suitable metal adapted to conduct high frequency electrical stimulation signals to the tissue T delivered from the power source 11. As shown in FIG. 3, housing end 14 defines longitudinal axis 20. Housing end 15 defines a second longitudinal axis 21 and, in the illustrated embodiment, axis 20 extends at an angle of approximately 45° to axis 21.

Head 18 further defines a swivel connection 22 for rotatably mounting the head to housing end 14 to swivel the head about axis 20. Thus, the swivel head may be selectively infinitely adjustable between a lowermost position, as shown in FIG. 3, and an uppermost position, as shown in FIG. 4, as desired by the user.

The swivel connector 22 includes a tubular insert 24 mounted in housing end 14 to project coaxially outwardly therefrom, and head 18 includes a mounting portion 25 rotatably mounted to the projecting outer portion 26 of the insert to provide a frictionally retained adjustable positioning of the head about axis 20.

The metal cap 19 is preferably grounded by a ground connection 27 to a tubular connector 28 in electrical conductive association with the cap, as shown in FIG. 3. When the cap is utilized as means for providing electrical stimulation to the patient's tissue T, high frequency current is delivered thereto through the connection 28.

Switch controls generally designated 29 are mounted to the housing 10 within grasping portion 16, as shown in FIG. 3. The switch control means 29 includes a plurality of switches 30 adapted to be operated by fingertip engagement by the user's fingers, with selected ones of switch areas 31 provided on a graphic overlay 32 on the housing, as seen in FIG. 2.

Cable 12 includes a switch cable 33 connected between the switch 32 and the power source 11. Cable 12 further includes a second power-conducting cable 34 connected between the tubular connector 28 and power source 11. Cable 2 may be secured to housing end 15 by a strain relief 35 rotatively mounted in a sleeve 38 disposed coaxially in the housing. Rotation and water tightness of the strain relief is controlled by an O-ring 37 and is limited by a stop 36, as shown in FIG. 3. Cable 33 is electrically connected to the leads 39 of switches 30 by a suitable connector 40. Thus, cable 34 is free to turn about its longitudinal axis when the head 18 is angularly positioned to prevent undesirable stressing of the cable.

Grasping portion 16 of the housing defines a generally C-shaped housing portion having one leg 41 thereof inclined in a first direction to access 21, and an opposite, second leg 42 inclined at an opposite angle to the axis. Thus, the C-shaped grasping portion defines a fingertip receiving space 43 adjacent the housing end 14 for facilitated manual positioning of the applicator head against the patient's tissue, without interference from the user's fingers grasping the applicator.

As further illustrated in FIG. 3, switches 30 are disposed in the first leg 41 of the grasping portion, and the housing is provided with a plurality of ribs 44 oppositely of the switches and graphic display 32 on the housing portion 41 for slip-free retention of the user's fingers in the use of the applicator. Thus, more specifically, the user may operate switches 30 by suitable depression of selected areas of the graphic display, while retaining the applicator firmly grasped by the embracing of the user's hand about the applicator housing portion 41. Additionally, the user has positive control of the applicator in pressing the head 18 against the patient's tissue. Still further, the positive retention of the applicator permits facilitated swiveling of the head to a desired angular position relative to axis 20, while firmly holding the housing portion 41 with one hand while adjusting the head.

Cable 34 may be brought outwardly through sleeve insert 24 which, as shown in FIG. 3, may have clearance with the cables. The sleeve is coaxially rotatable in the housing end and locked against axial displacement from the housing end 14 by a set screw 45 cooperating with an annular groove 46 in the sleeve. The electrical conductors 47 of cable 38 are brought through the mounting portion 45 of the head to the transducer 17 and ground connection 27 for facilitated swivelling of the head about the axis 20, while maintaining the electrical connections.

An indicator 58 may be provided in the graphic display and, in the illustrated embodiment, comprises a light-emitting diode indicator at the front end of the graphic display adjacent the switch areas 31, as shown in FIG. 5. Illustratively, the indicator may be connected to the power source to indicate when the power source is energized. As will be obvious to those skilled in the art, other indicators may be used in conjunction with the control, as desired.

As will further be obvious to those skilled in the art, the selective energization of the transducer or cap for providing ultrasonic mechanical vibration physiological effects in the patient's tissue or electrical stimulation thereof may be effected by any suitable form of power supply and control means mounted in the grasping portion of the housing within the broad scope of the invention. In the illustrated embodiment, as shown in FIG. 5, the control includes four switches 49, 50, 51, and 52, operated one each by the switch actuation portions 31 of the overlay 32.

Thus, as illustrated in FIG. 6, each of switches 49, 50, 51 and 52 comprises a normally open switch connected to the power supply by a common lead 53 and control leads 54, 55, 56, and 57, respectively. LED 58 is connected to the power supply by leads 59 and 60. A selector switch 61 may be provided on the power supply for selective use of the apparatus as a mechanical vibration applicator or an electro-stimulation applicator. Thus, the control provided by switches 49 and 50 may be selectively utilized to energize the power supply to provide suitable electrical signals for effecting operation of the transducer crystal 17 to provide ultrasonic vibration of the patient's tissue, or to provide high frequency electrical signals to the cap 19 to provide electrical stimulation of the patient's tissue.

In the illustrated embodiment, switches 49 and 50 are connected so as to provide different power levels of the signal from the power supply to the applicator head, and switches 51 and 52 are arranged to control the power supply to provide preselected discrete different frequencies. In the illustrated embodiment, the switch 49 causes an increase in the power level, whereas switch 50 controls a decrease in the power level so as to provide an infinite adjustability of the power to the applicator head. As will be obvious to those skilled in the art, the frequency control means may similarly comprise means for providing an infinite adjustability of the frequency of the signal provided to the applicator head.

In the use of the apparatus as a mechanical vibration applicator, the switches are connected through cable 12 to a conventional microprocessor controller 62 of the power source 11. Such processor controllers are well-known to those skilled in the art and require no further description herein.

The power source further includes an RF amplifier and oscillator of conventional construction, generally designated 63. Such RF amplifiers and oscillators are similarly well-known to those skilled in the art and require no further elaboration herein.

The power cable 34 is connected between the amplifier oscillator portion 63 of the power source and the applicator head and, as shown in FIG. 6, the ground portion of the cable is connected at 64 to the cap of the applicator head. The amplifier oscillator is connected, in addition, through the cable 34 to the crystal transducer 17.

Thus, by suitable controlled manipulation of the switches 49-53, both the power level and frequency characteristics of the mechanical vibrations produced by transducer 17 is effected by the user's hand grasping the applicator grasping portion and urging the applicator head against the patient's tissue. There is no need for the user of the apparatus to return to the power source for adjusting these parameters and, thus, improved, facilitated stimulation and/or treatment of the patient's tissue may be effected by the user.

Additionally, the swivel mounting of the applicator head to the housing end 14 permits facilitated application of the physiological signals to the tissue by permitting facilitated facial engagement of the planar outer surface 65 of the cap 19 against the patient's tissue As discussed above, the grasping portion defines a fingertip receiving space 43 preventing interference between the user's hand and the tissue so as to permit facilitated facial engagement of the applicator with the tissue.

As the grasping portion is disposed immediately adjacent the housing end 14, direct application of the physiological stimulation effect is afforded to the user.

The facilitated adjustment of the parameters of the applied physiological stimulation permits continuous adjustment thereof when desired in directing the treatment to different portions along the surface of the tissue.

The provision of the frictional fingertip contact means 44 assures a positive control of the retention of the applicator during the use thereof to permit precise control of the physiological treatment application.

The applicator is extremely light in weight for further facilitated application of the physiological treatment vibrations or oscillations.

Where the apparatus is utilized for providing electrostimulation of the tissue, the power source includes an electrostimulation amplifier 66. Suitable electrodes 67 may be applied to the user's skin and connected to the electrostimulation amplifier by a conductor 68. The conductor 69 of the cable, as discussed above, may be connected to the ground connection 64, whereby suitable electrical stimulation of the tissue may be effected by conduction through the tissue between electrodes 67 and ground connection 64 placed in electrical conduction engagement with the patient's tissue through the cap 19.

Switch 61 may be selectively positioned to provide for mechanical vibration use of the transducer or electrostimulation use of the cap under the control of the switches 29 carried by the housing grasping portion in the use of the apparatus.

The invention comprehends that the light-emitting diode 58 may be utilized to indicate the actual coupling of the ultrasonic signal to the patient's tissue by suitable means in the power source. Such indicating signal means are well-known to those skilled in the art and require no further description herein.

Figure 7:
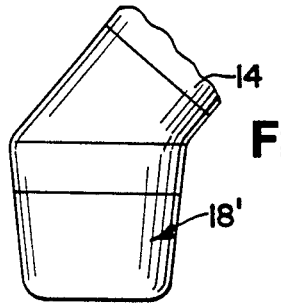
FIG. 7 is a fragmentary side elevation of a modified form of head for use in the applicator.
Figure 8:
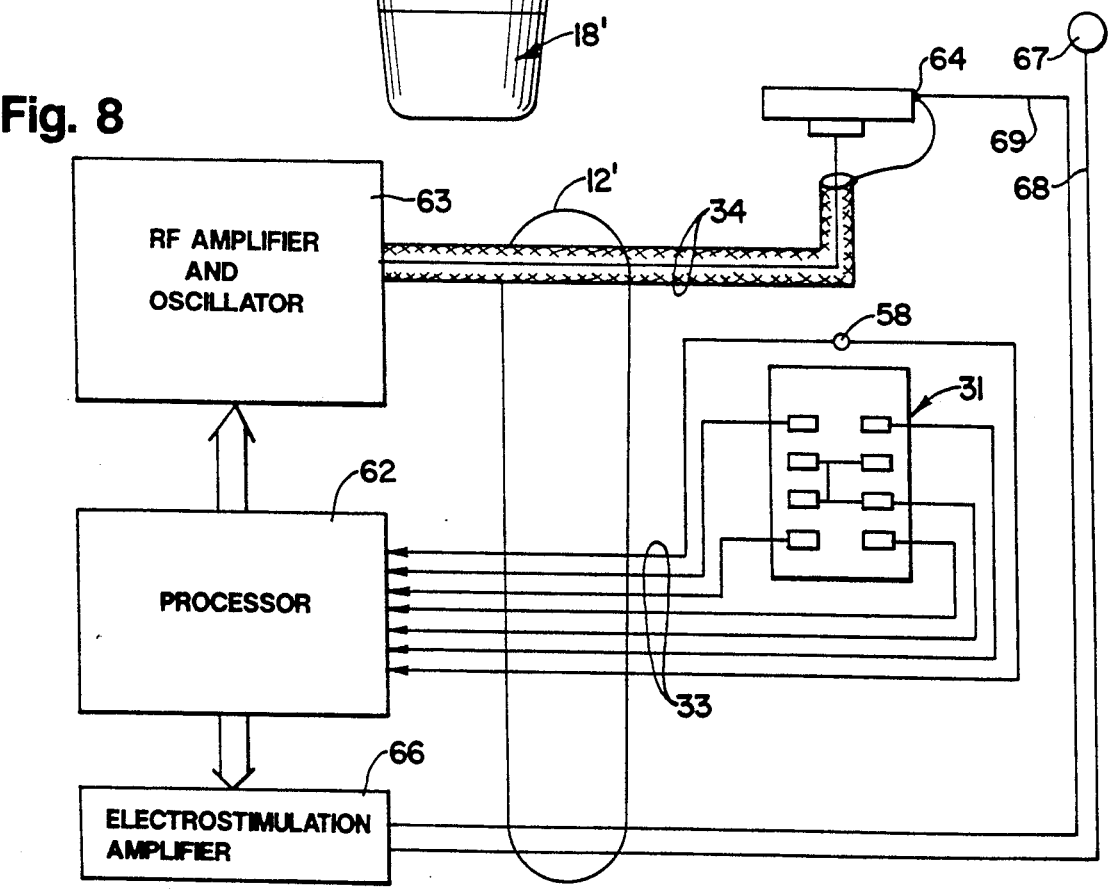
FIG. 8 is a schematic electrical diagram illustrating a modified form of the invention wherein the applicator may be alternatively utilized as an applicator for providing electrical stimulation of the physiological tissue.

As indicated briefly above, the physical construction of the head of the applicator may be varied as desired to provide a wide range of applications for the apparatus. Thus, as illustrated in FIG. 7, a reduced diameter head 69 may be utilized in lieu of the relatively large diameter swivel head 18 illustrated in FIGS. 2 and 3.

The invention broadly comprehends the provision of a hand-held applicator having variable control elements in a grasping portion thereof for selectively providing physiological stimulation signals to a patient's tissue under the control of the user by fingertip manipulation of the control means in the applicator grasping portion. The invention comprehends the provision of such an applicator for use in providing different forms of physiological stimulation to a patient's tissue. The invention further comprehends the provision of means for facilitating facial engagement of the applicator head with the patient's tissue by providing a swivelling mounting of the head to the end of the applicator housing.

The foregoing disclosure of specific embodiments is illustrative of the broad inventive concepts comprehended by the invention.

We claim:

1. Manually operable apparatus for controlled physiological stimulation of tissue, comprising:
    an elongated housing having a first end defining an axis, an opposite second end, and a housing grasping portion intermediate said ends;
    an electrically operable transducer;
    mounting means for mounting said transducer to said first housing end comprising means for directing said transducer at an angle to said axis selectively at any one of a plurality of positions circumferentially about said axis; and
    means for energizing said transducer including a power source spaced from said housing, manually operable controls at said housing grasping portion, and electrical conductors for interconnecting said power source, controls, and transducer to permit concurrent controlled energization and physical positioning of said transducer by a user's hand embracing said housing grasping portion.

2. The manually operable apparatus of claim 1 wherein said controls comprise means for controlling the power delivered to said transducer from said power source.

3. The manually operable apparatus of claim 1 wherein said power source comprises means for providing alternating current to said transducer at any one of a plurality of different frequencies, and said controls comprise means for controlling the frequency of the power delivered to said transducer from said power source.

4. The manually operable apparatus of claim 1 wherein said power source comprises means for providing alternating current to said transducer at any one of a plurality of different frequencies, and said controls comprise means for controlling the frequency of the power delivered to said transducer from said power source and for controlling the power delivered to said transducer from said power source.

5. The manually operable apparatus of claim 1 wherein said angle is substantially 45°.

6. The manually operable apparatus of claim 1 wherein said transducer defines a planar tissue-engaging surface extending at an angle of substantially 45° to said axis.

7. The manually operable apparatus of claim 1 wherein said grasping portion defines an axis extending substantially perpendicular to said first end axis.

8. The manually operable apparatus of claim 1 wherein said power source comprises means for operating said transducer to provide mechanical vibration of tissue against which said transducer is urged.

9. The manually operable apparatus of claim 1 wherein said power source comprises means for operating said transducer to provide electrical energy stimulation of tissue against which said transducer is urged.

10. The manually operable apparatus of claim 1 wherein said power source comprises means for operating said transducer to provide selectively mechanical vibration of tissue against which said transducer is urged and/or electrical energy stimulation of tissue against which said transducer is urged.

11. Manually operable apparatus for controlled physiological stimulation of tissue, comprising:
an elongated housing having a first end defining an axis, an opposite second end, and a grasping portion intermediate said ends;
an electrically operable transducer;
mounting means for mounting said transducer to said first housing end selectively at any one of a plurality of positions circumferentially about said axis; and
means for energizing said transducer including a power source spaced from said housing, manually operable controls at said housing grasping portion, and electrical conductors for interconnecting said power source, controls, and transducer to permit controlled energization and physical positioning of said transducer.

12. The manually operable apparatus of claim 11 wherein said controls comprise means for controlling the power delivered to said transducer from said power source.

13. The manually operable apparatus of claim 11 wherein said power source comprises means for providing alternating current to said transducer at any one of a plurality of different frequencies, and said controls comprise means for controlling the frequency of the power delivered to said transducer from said power source.

14. The manually operable apparatus of claim 11 wherein said power source comprises means for providing alternating current to said transducer at any one of a plurality of different frequencies, and said controls comprise means for controlling the frequency of the power delivered to said transducer from said power source and for controlling the power delivered to said transducer from said power source.

15. The manually operable apparatus of claim 11 wherein said controls comprise means for selectively providing power from said power source to said transducer at any one of a plurality of discrete different power levels.

16. The manually operable apparatus of claim 11 wherein said power source comprises means for providing alternating current to said transducer at any one of a plurality of different frequencies, and said controls comprise means for selectively providing power from said power source to said transducer at any one of a plurality of discrete different frequencies.

17. The manually operable apparatus of claim 11 wherein said power source comprises means for operating said transducer to provide mechanical vibration of tissue against which said transducer is urged.

18. The manually operable apparatus of claim 11 wherein said power source comprises means for operating said transducer to provide electrical energy stimulation of tissue against which said transducer is urged.

19. The manually operable apparatus of claim 11 wherein said power source comprises means for operating said transducer to provide selectively mechanical vibration of tissue against which said transducer is urged and/or electrical energy stimulation of tissue against which said transducer is urged.

20. Manually operable apparatus for controlled physiological stimulation of tissue, comprising:
an elongated housing having a first end defining an axis, an opposite second end, and a grasping portion intermediate said ends;
an electrically operable transducer;
mounting means for mounting said transducer to said first housing end comprising means for directing said transducer at an angle to said axis selectively at any one of a plurality of positions circumferentially about said axis; and
means for energizing said transducer including a power source, manually operable controls, and electrical conductors for interconnecting said power source, controls, and transducer to permit physical positioning of said transducer by a user's hand embracing said housing grasping portion, with said transducer positioned at a preselected angle to said axis.

21. The manually operable apparatus of claim 20 wherein said mounting means comprises means for infinitely adjusting the position of said transducer about said axis.

22. The manually operable apparatus of claim 20 wherein said transducer defines a planar tissue-engaging surface extending at an angle of substantially 45° to said axis, and said mounting means comprises means for infinitely adjusting the position of said transducer about said axis.

23. The manually operable apparatus of claim 20 wherein in said grasping portion defines an axis extending substantially perpendicular to said first end axis.

24. The manually operable apparatus of claim 20 wherein said housing grasping portion includes means defining an irregular grasping surface for improved slip-free grasping of said grasping portion by the user.

25. The manually operable apparatus of claim 20 wherein said housing opposite second end defines a longitudinal second axis, and said first end axis extends at a preselected angle to said second axis.

26. The manually operable apparatus of claim 20 wherein said housing grasping portion defines a C-shaped housing portion providing a fingertip receiving space adjacent said housing first end.

27. The manually operable apparatus of claim 20 wherein in said power source comprises means for operating said transducer to provide mechanical vibration of tissue against which said transducer is urged.

28. The manually operable apparatus of claim 20 wherein said power source comprises means for operating said transducer to provide electrical energy stimulation of tissue against which said transducer is urged.

29. The manually operable apparatus of claim 20 wherein said power source comprises means for operating said transducer to provide selectively mechanical vibration of tissue against which said transducer is urged and/or electrical energy stimulation of tissue against which said transducer is urged.

* * * * *